(12) United States Patent
Bernhardt et al.

(10) Patent No.: US 7,436,930 B2
(45) Date of Patent: Oct. 14, 2008

(54) METHOD FOR CONTROLLING THE DOSE OR THE DOSE RATE WHEN RECORDING X-RAY IMAGES

(75) Inventors: Philipp Bernhardt, Forchheim (DE);
Stefan Böhm, Oberasbach (DE);
Bernhard Geiger, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 86 days.

(21) Appl. No.: 11/402,329

(22) Filed: Apr. 11, 2006

(65) Prior Publication Data
US 2006/0233304 A1      Oct. 19, 2006

(30) Foreign Application Priority Data
Apr. 15, 2005   (DE)   ................. 10 2005 017 489

(51) Int. Cl.
*H05G 1/38* (2006.01)
*H05G 1/46* (2006.01)
(52) U.S. Cl. ................ 378/97; 378/98.7; 378/108
(58) Field of Classification Search .............. 378/97, 378/98.7, 108
See application file for complete search history.

(56) References Cited
U.S. PATENT DOCUMENTS

| | | | | |
|---|---|---|---|---|
| 3,492,483 A | * | 1/1970 | Batki et al. | 378/108 |
| 5,485,501 A | * | 1/1996 | Aichinger | 378/98.7 |
| 5,710,801 A | * | 1/1998 | Dillen et al. | 378/98.7 |
| 6,018,565 A | * | 1/2000 | Ergun et al. | 378/95 |
| 6,229,875 B1 | * | 5/2001 | Keesmaat | 378/98.7 |
| 6,333,965 B1 | * | 12/2001 | Van Berkel | 378/98.7 |
| 6,744,849 B2 | * | 6/2004 | Nagatsuka | 378/62 |
| 6,813,335 B2 | * | 11/2004 | Shinbata | 378/62 |
| 7,120,229 B2 | * | 10/2006 | Takasawa | 378/98.2 |
| 2004/0228443 A1 | * | 11/2004 | Bohm et al. | 378/97 |
| 2006/0002513 A1 | * | 1/2006 | Bernhardt et al. | 378/97 |
| 2007/0076937 A1 | * | 4/2007 | Spahn | 382/132 |
| 2007/0081722 A1 | * | 4/2007 | Friedrich | 382/168 |

FOREIGN PATENT DOCUMENTS

| | | | |
|---|---|---|---|
| DE | 103 11 627 A1 | 9/2004 | |
| JP | 06275394 A | * 9/1994 | ................. 378/62 |

* cited by examiner

*Primary Examiner*—Edward J Glick
*Assistant Examiner*—Thomas R Artman

(57) ABSTRACT

With a method for controlling the dose or dose rate when recording x-ray images by means of a detector comprising image elements which record a plurality of dose data values, an actual value is determined for the dose or dose rate from the totality of the data values recorded by the image elements of a predetermined image segment, said actual value being compared with a predetermined target value in order to control the dose or dose rate when recording a further x-ray image. In accordance with the invention, the actual value is determined such that on the basis of a frequency distribution of the dose data values of the image elements assigned to the dominant, a p-quantile is determined, and that the dose data value assigned to the p-quantile is used to determine the actual value.

8 Claims, 1 Drawing Sheet

METHOD FOR CONTROLLING THE DOSE OR THE DOSE RATE WHEN RECORDING X-RAY IMAGES

CROSS REFERENCE TO RELATED APPLICATIONS

This application claims priority to the German Application No. 10 2005 017 489.2, filed Apr. 15, 2005 which is incorporated by reference herein in its entirety.

FIELD OF INVENTION

The invention relates to a method for controlling the dose or dose rate when recording x-ray images by means of a detector comprising image elements which record a plurality of dose data values. The detector is thereby made up of these image elements, with the dose data values being displayed as gray values, thereby resulting in an image. A dose data value reproduces the dose of x-rays received by the image element, with the detector receiving the radiation of an x-ray tube, which preradiates the object of the x-ray recording (e.g. the patient).

BACKGROUND OF INVENTION

It is known in the prior art to determine the dose or the dose rate in order to control the voltage of the x-ray tube, of the x-ray tube current, of the exposure duration and/or in order to control a prefiltering from an initially recorded x-ray image. For this purpose, an image segment (dominant) is selected from the initially recorded x-ray image and the data assigned to this image segment is used to determine an actual value for the dose or dose rate. This data relates to the totality of the data values recorded by the image elements assigned to the dominant. To control the dose or dose rate when recording a further x-ray image, the determined actual value is compared with a predetermined target value, and a corresponding change in the control variables takes place. In the case of the exposure time this is a proportional variable. In other words, the exposure time is doubled for instance, if the actual value is only half as great as the target value.

The object of an operator has hitherto been to select the dominant as an image segment. The dominant should comprise typical image segments and the dose or dose rate for the subsequent x-ray recording is optimized to this dominant. An average dose data value from the image elements of the dominant has hitherto been used as the actual value for the dose or dose rate.

In particular, if the dominant of the initially recorded x-ray image comprises regions of direct radiation, i.e. regions in which the radiation emitted from the x-ray tube directly hits the detector, without being absorbed to a significant degree by the object of the image, the average dose of the x-rays received by the image elements of the dominant increases. If an actual value is determined from this increased dose, a control can result in the actual value having to be reduced to a target value. Consequently, the subsequent image is less significantly exposed. This results in a deterioration of the image quality, particularly in significantly absorbent regions.

A method for determining a characteristic for the dose is known from DE 103 11 627 A1, in which the median of the dose data values from a region of interest is used as the characteristic. The median is a value, above and below which half of the data values lie respectively, with said median generally differing from a simple average value.

The treating doctor has thus hitherto been in favor of aligning the dominant to the significantly absorbing regions so as to achieve the best possible contrast. Dominants featuring an image region, in which the direct radiation is significant, generally result in a dose which is too low in the next recorded x-ray image.

SUMMARY OF INVENTION

An object of the invention is to eliminate the problem in that the selection of the dominant by an operator is further decisive for the quality of the images.

This object is achieved by the claims.

The method implies that a p-quantile is determined on the basis of a frequency distribution of the dose data values of the image elements assigned to the dominant, and that the dose data value assigned to the p-quantile serves to determine the actual value.

A p-quantile is a number which divides a frequency distribution with n entries into a specific ratio. In the case of a p-quantile, with 0<p<1, n*p entries are smaller than the p-quantile and (1−p)*n entries are greater than the p-quantile. A 0.5-quantile is the median.

The p-quantile with the invention can now be selected according to the first alternative such that the control is geared to the dose data value in significantly absorbent regions of the dominant, i.e. to the received dose in the regions of the image which are of particular interest for a high-contrast display. The p-value can be selected in an examination-dependent manner, for instance can be dependent upon whether the hand of a patient or the thorax is being x-rayed.

According to a second alternative or in addition, the p-value can be provided particularly interactively by an operator, i.e. changeable from x-ray to x-ray, and can be input into the x-ray recording system via a keyboard for instance.

A p-value of 20% (0.2-quantile) allows a dominant to be selected, which still features a certain amount of direct radiation, provided this direct radiation does not exceed 80% of the image proportion. The invention thus enables the dominant to be selected more liberally, provided only the p-quantile is defined as adequate.

In particular it is possible that the essentially complete image is selected as a dominant, i.e. that the selection of a dominant which still merits this name is de facto completely obviated. With a preferred embodiment, the complete image is selected as a dominant by removing a predetermined frame-like boundary (for the removal of the image aperture region).

The determination of the actual value on the basis of a p-quantile allows the direct radiation to be suitably considered by means of a suitable selection of the p-value such that the selection of a dominant is no longer decisive, but instead the correct specification of the p-value.

BRIEF DESCRIPTION OF THE DRAWINGS

A preferred embodiment of the invention is now described with reference to the drawing, in which:

FIG. 1 shows the frequency distribution of a typical x-ray image with a relatively high amount of direct radiation and FIG. 2 explains the selection of a dominant which is possible from now on.

DETAILED DESCRIPTION OF INVENTION

Figure 1:
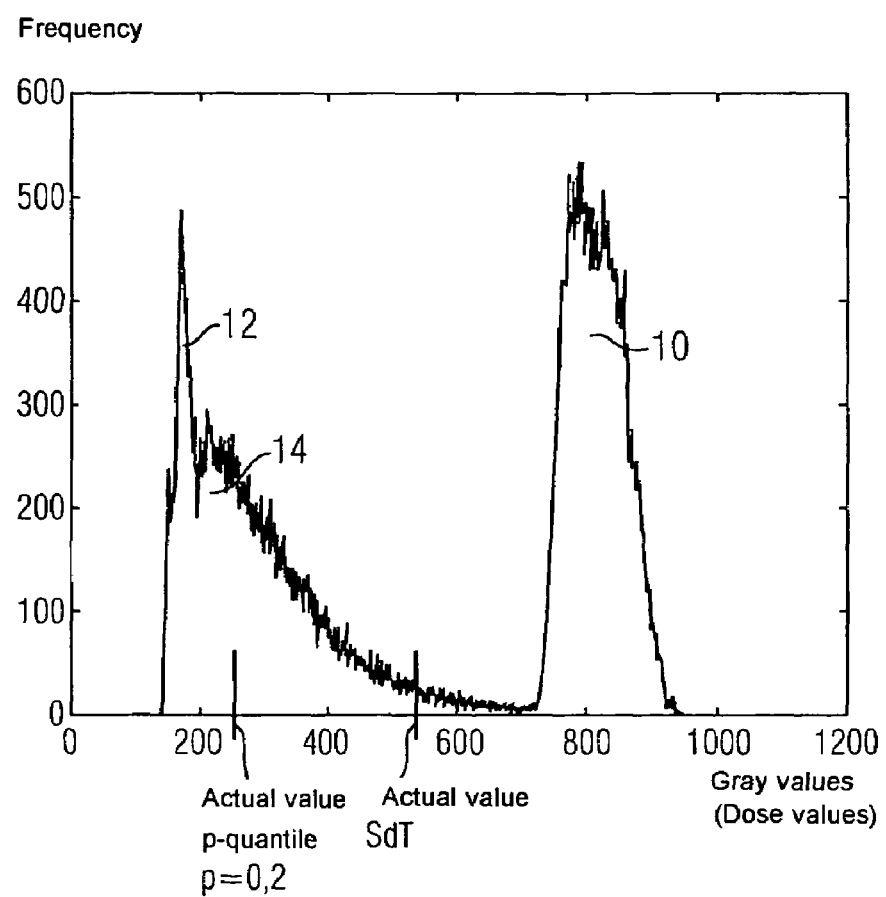

FIG. 1 shows the frequency of specific gray values in an initially recorded x-ray image in a typical situation. The gray values correspond to dose values determined in the image, said dose values having been recorded by the individual pixels (image elements) of the x-ray detector.

With high dose values, the frequency distribution visibly comprises a first peak 10. This first peak 10 represents the direct radiation, i.e. x-rays, which directly hit the detector without having been absorbed or x-rays which have penetrated extremely weakly absorbent regions of an image object.

With extremely low dose values, the x-rays comprise a second peak 12. These are dose values which correspond to significantly absorbing regions of the image, bones of a patient for instance, in particular their spinal columns etc.

If the simple average value is now taken from the data displayed in the frequency distribution as the actual value for the control of the next x-ray recording, an actual value results according to the prior art (actual value Sdt) of approximately 550. This actual value is naturally pushed upwards as far as possible by the peak 10, which is very wide, so that it departs considerably from the significantly absorbent peak 12. Accordingly, the dose of the subsequent x-ray image is controlled on the basis of a too high actual value per se, such that the subsequent x-ray image is presumably exposed too weakly to adequately image the region of significant absorptions.

The invention now allows the actual value to be formed in another manner. A value of approximately 225 is reached as an actual value for a p-quantile of p=0.2. This value lies directly above the peak 12 of the significantly absorbed radiation and still lies in the region of an adjacent peak 14, in which the radiation is still relatively significantly absorbed. If the dose or dose rate of the subsequent x-ray image is controlled on the basis of this actual value, the direct radiation according to peak 10 no longer plays an important role and the region of significantly absorbent radiation directly determines the control of the exposure of the subsequent x-ray image, so that this region is particularly well imaged.

As the peak 10 in a way no longer plays a role due to the use of a suitable p-quantile, it is possible to dispense with selection of a dominant as such by the user (i.e. the radiologist recording the images). Instead, the overall image can essentially be used to determine a frequency distribution according to FIG. 1. An interference first occurs if the region of the peak 10 is so significant that it moves into the p-quantile. In this case, the amount of direct radiation is already too high.

Figure 2:
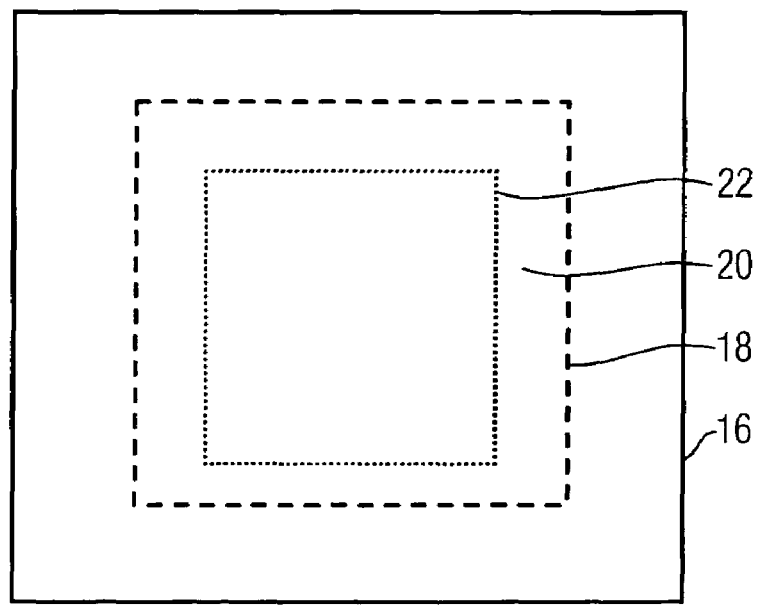

FIG. 2 now shows the surface of a detector 16 which is made of image elements which record dose data values in each instance. Since a part of the image is masked out, the contour 18 of the aperture is displayed using a dashed line. The entire region 20 in the interior of the contour 18 can be taken per se as dominant. As a precaution, the dominant is restricted to a region 22 which is indicated in its contour with a dotted line, and is suitable with the known aperture position. The region 22 is determined on the basis of a data value detected by the aperture position. The region 22 represents a 'universal dominant', which essentially comprises the overall image by removing a predetermined flame-like boundary. As described above with reference to FIG. 1, the direct radiation no longer plays an interfering role as a result of a suitable fixing of the p-value for a p-quantile, so that the dominant 22 can be used in all cases and only the p-value for the p-quantile must be suitably selected.

A typical p-value of 0.2 is shown in FIG. 1. The invention is however not fixed to this value. The necessary p-value can be subject to significant fluctuations depending on the examination. In the case of an examination of the thorax for instance, in which a large number of bones are imaged together, a large image region is significantly absorbent so that the p-value can be set to 0.8 (80% quantile for determining the actual value). In contrast, in the case of imaging a human hand, the regions of the direct radiation are particularly significantly distinctive, so that a p-value of 0.2 or even smaller (20% quantile) must be selected.

Since the p-value can fluctuate depending on the examination, provision is made with a preferred embodiment that the doctor operating the system inputs the p-value into the x-ray system via a keyboard (not shown) or another operating element, and in this x-ray system the control is then carried out on the basis of a p-quantile with reference to the inputted p-value.

The invention claimed is:

1. A method of controlling a dose or a dose output while recording x-ray images using an x-ray detector comprising image elements configured to record a plurality of dose data values, the method comprising:
    selecting a dominant having a plurality of image elements from a previously recorded x-ray image;
    determining an actual dose or dose output value based on the plurality of dose data values related to the plurality of image elements;
    prescribing a voltage, current or exposure value to set the actual dose or dose output value; and
    recording an x-ray image using the set dose or set dose output value wherein the step of determining the actual dose or dose output value includes:
    determining a frequency distribution from the plurality of dose data values related to the plurality of image elements;
    determining a p-quantile based on the frequency distribution;
    determining a further dose data value from the p-quantile; and
    determining the actual dose or dose output value based on the further dose data value.

2. The method according to claim 1, wherein the p-quantile is determined from such parts of the frequency distribution corresponding to highly absorbing regions of the dominant.

3. The method according to claim 1, wherein the p-quantile is input by a user.

4. The method according to claim 1, wherein the dominant includes the previously recorded x-ray image as a whole.

5. The method according to claim 1, wherein the dominant includes the previously recorded x-ray image excluding a border area of the previously recorded x-ray image.

6. The method according to claim 5, wherein the border area is determined from an aperture of the x-ray detector.

7. A method according to claim 1, wherein the control algorithm effects a voltage of an x-ray tube, a current of the x-ray tube, an exposure of the x-ray detector.

8. A method according to claim 7, wherein the control algorithm includes a pre-filtering algorithm.

* * * * *